(12) United States Patent
Amer et al.

(10) Patent No.: US 12,228,547 B2
(45) Date of Patent: Feb. 18, 2025

(54) ONLINE INSPECTION FOR EARLY HTHA DETECTION USING A HYBRID SENSORY SYSTEM

(71) Applicant: Saudi Arabian Oil Company, Dhahran (SA)

(72) Inventors: Ayman Amer, Thuwal (SA); Abdulwahab A. Halawani, Jeddah (SA)

(73) Assignee: Saudi Arabian Oil Company, Dhahran (SA)

( * ) Notice: Subject to any disclaimer, the term of this patent is extended or adjusted under 35 U.S.C. 154(b) by 351 days.

(21) Appl. No.: 17/715,515

(22) Filed: Apr. 7, 2022

(65) Prior Publication Data

US 2023/0324339 A1     Oct. 12, 2023

(51) Int. Cl.
*G01N 27/904* (2021.01)
*G01N 27/90* (2021.01)
*G01N 33/00* (2006.01)
*G01N 33/207* (2019.01)

(52) U.S. Cl.
CPC ....... *G01N 27/904* (2013.01); *G01N 27/9046* (2013.01); *G01N 33/0075* (2013.01); *G01N 33/207* (2019.01)

(58) Field of Classification Search
CPC ........... G01N 33/0075; G01N 27/9046; G01N 33/207; G01N 27/904
See application file for complete search history.

(56) References Cited

U.S. PATENT DOCUMENTS

| 4,685,334 A * | 8/1987 | Latimer | G01N 29/11 |
| | | | 73/622 |
| 5,404,754 A * | 4/1995 | Wang | G01N 29/4463 |
| | | | 73/598 |
| 6,019,943 A | 2/2000 | Buscemi et al. | |
| 6,125,704 A | 10/2000 | Wang | |

(Continued)

FOREIGN PATENT DOCUMENTS

EP          3862738       8/2021
WO     WO 2021102079     5/2021

*Primary Examiner* — Catherine T. Rastovski
*Assistant Examiner* — Sharad Timilsina
(74) *Attorney, Agent, or Firm* — Fish & Richardson P.C.

(57) ABSTRACT

Systems and methods include a computer-implemented method for inspection. Sensors are installed on locations susceptible to high temperature hydrogen attack (HTHA) on equipment used in hydrocarbon facilities. Attachment uses adaptable hybrid pads. Surface data captured using permanent sensors includes surface temperatures, per hydrogen (pH) measurements, and methane measurements for methane escaping from external surfaces of the equipment. Stress cracks in the equipment base metal are detected. An HTHA susceptibility analysis of the equipment is performed based on the presence of the cracks and by analyzing surface data and mapping potential HTHA cracks and locations of early signs of methane formation, including monitoring heat-affected zones (HAZ) and fusion lines of welds. Locations of the detected stress cracks caused by HTHA in metals are determined. An inspection result and assessment are generated, including a final analysis of assessment reports indicating a likelihood of cracks propagation and fissuring inside the equipment base metal.

20 Claims, 9 Drawing Sheets

(56) References Cited

U.S. PATENT DOCUMENTS

| | | | |
|---|---|---|---|
| 6,193,876 B1* | 2/2001 | Manolatos | B01J 3/048 |
| | | | 208/366 |
| 2016/0103099 A1* | 4/2016 | Lott | G01N 27/904 |
| | | | 324/242 |
| 2018/0335404 A1 | 11/2018 | Amer et al. | |
| 2019/0360974 A1* | 11/2019 | Barshinger | G01N 29/11 |
| 2020/0286215 A1 | 9/2020 | Brill et al. | |
| 2021/0284923 A1 | 9/2021 | Koseoglu et al. | |
| 2022/0196530 A1* | 6/2022 | Kinyon | G01N 3/56 |
| 2023/0324339 A1 | 10/2023 | Amer et al. | |

* cited by examiner

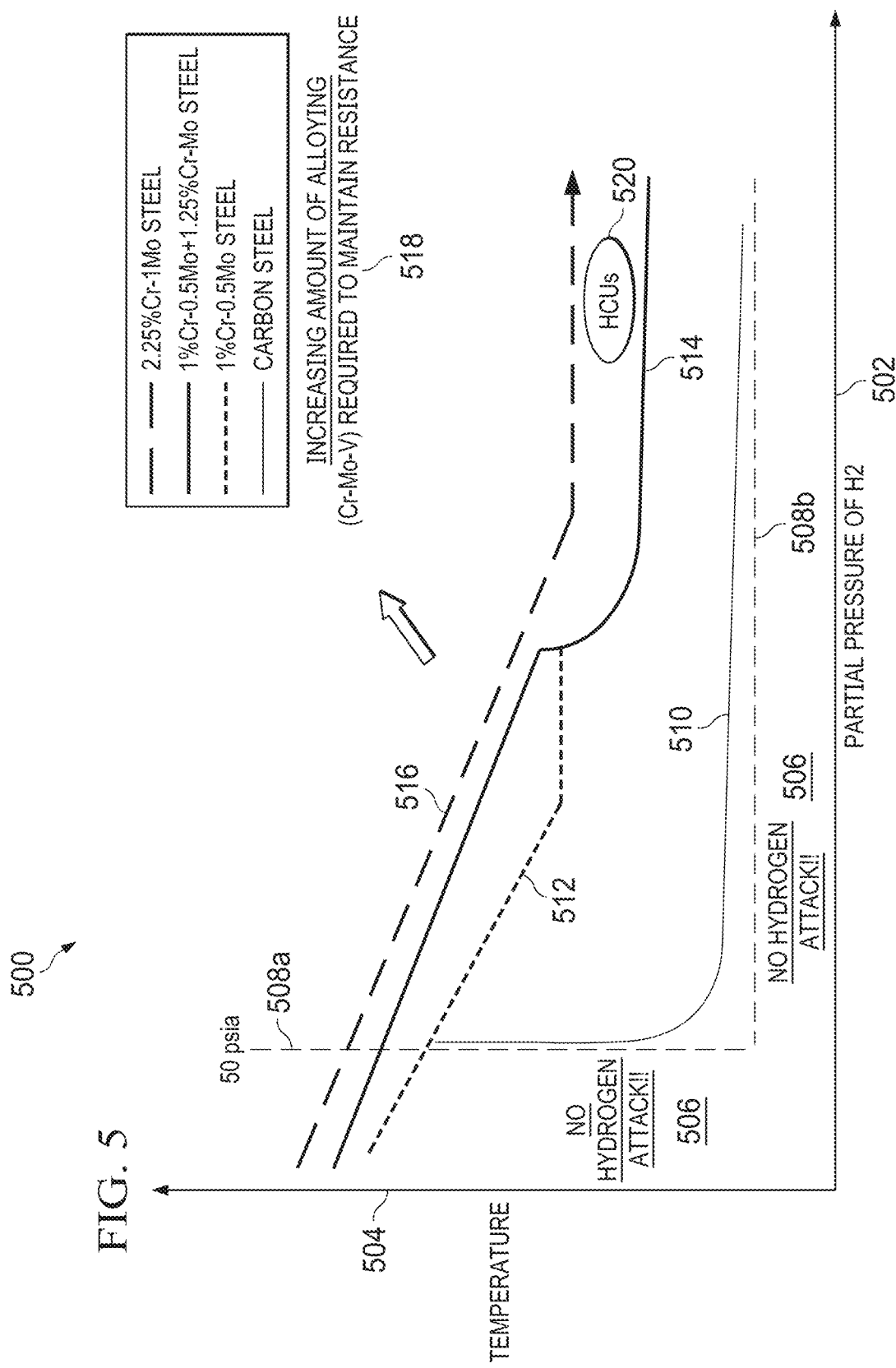

ONLINE INSPECTION FOR EARLY HTHA DETECTION USING A HYBRID SENSORY SYSTEM

TECHNICAL FIELD

The present disclosure applies to inspections of equipment used in the gas and oil industry.

BACKGROUND

Remote and online inspection techniques can be used in the oil and gas industry to achieve higher efficiency and improved integrity. For example, the detection and mitigation of high-temperature hydrogen attack (HTHA) has been highlighted by facilities throughout the oil and gas sector as a critical inspection challenge, affecting potential financial losses and safety concerns. HTHA commonly occurs in process equipment that is exposed to hydrogen at high temperatures and pressures. Typical vulnerable assets include heat exchangers, piping equipment, and pressure vessels. The rapid deterioration of assets caused by HTHA is known to lead to process shutdowns of units and, in some cases, entire facilities.

HTHA is also a major issue in the refining and petrochemical industries. HTHA can occur in carbon and low-alloy steels which are exposed, for example, to a high partial pressure of hydrogen at elevated temperatures. In these types of cases, HTHA is the result of atomic hydrogen diffusing through the steel and reacting with carbides in the microstructure. This type of atomic hydrogen interacts with carbon to form methane gas. Since methane is a larger molecule and unable to diffuse out of the steel, pressure increases caused by the methane molecules typically form fissures and cracks.

Damage which occurs due to HTHA can be in the form of either internal decarburization and fissuring, surface decarburization, or both. Internal decarburization and fissuring results from the accumulation of methane gas at the carbide matrix interface. Surface decarburization results from the reaction of the atomic hydrogen with carbides at or near the surface where the methane gas can escape without causing fissures. Internal fissuring is more typically observed in carbon steel, e.g., C-½Mo steels and in Cr—Mo steels at higher hydrogen partial pressures. Surface decarburization is more commonly observed in Cr—Mo steels at higher temperatures and lower hydrogen partial pressures.

The early detection of HTHA is challenging. Current practices for HTHA detection are based on the use of conventional ultrasonic techniques. However, existing methodologies are insufficient in identifying HTHA potential damage while equipment is in use.

HTHA is of major concern in the refining and petrochemical Industry. HTHA occurs in carbon and low alloy steels exposed to a high partial pressure of hydrogen, operated at elevated temperatures (e.g., up to 900° F. (480° C.)). This anomaly can occur as a result of hydrogen diffusing through the steel and reacting with carbides in the microstructure. The hydrogen interacts with carbon to form methane gas. As methane is a larger molecule and unable to diffuse out of the steel, pressure increases can form fissures and cracks.

SUMMARY

The present disclosure describes techniques that can be used for using sensors to detect High Temperature Hydrogen Attack (HTHA) conditions in oil and gas (O&G) operations.

In some implementations, a computer-implemented method includes the following. Sensors are initiated that are installed at locations on equipment base metal of equipment used in hydrocarbon facilities. The locations include locations identified as susceptible to high temperature hydrogen attack (HTHA). The sensors are attached to the equipment using adaptable hybrid pads. Surface data is captured using the permanent sensors. The surface data includes surface temperatures, per hydrogen (pH) measurements, and methane measurements for methane escaping from external surfaces of the equipment. Stress cracks in the equipment base metal are detected using the surface data. An HTHA susceptibility analysis of the equipment is performed based, at least in part, on the presence of the cracks and by analyzing the surface data and mapping potential HTHA cracks and locations of early signs of methane formation, including monitoring heat-affected zones (HAZ) and fusion lines of welds. Locations of the detected stress cracks caused by HTHA in metals that are susceptible to HTHA are determined. An inspection result and assessment are generated using the captured surface data for presentation online, including a final analysis of assessment reports indicating a likelihood of cracks propagation and fissuring inside the equipment base metal.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method, the instructions stored on the non-transitory, computer-readable medium.

The subject matter described in this specification can be implemented in particular implementations, so as to realize one or more of the following advantages. Techniques of the present disclosure can be used to solve the technical problem of inspection. For example, the techniques can be used to provide an online inspection sensing technique applicable in harsh environments capable of inspecting and detecting micro-cracking for early prediction of HTHA. Also, the techniques can provide risk-based inspection (RBI) of damaged mechanisms and can provide continuous monitoring associated with asset integrity. The techniques can provide an online inspection sensing technique applicable in harsh environments capable of inspecting and detecting stress-cracking for early prediction of HTHA with high-temperature adhesive mechanisms. The techniques can provide an apparatus that can be installed at different locations. The techniques can provide the use of dry-coupled sensors to provide an online integrity assessment and to detect stress cracking associated with HTHA. The techniques can provide on-demand asset integrity for the material associated with this challenge (HTHA).

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

FIG. 5 is a diagram illustrating a representation of American Petroleum Institute (API) recommended practice (RP) Nelson curves, according to some implementations of the present disclosure.

Like reference numbers and designations in the various drawings indicate like elements.

DETAILED DESCRIPTION

Figure 1:
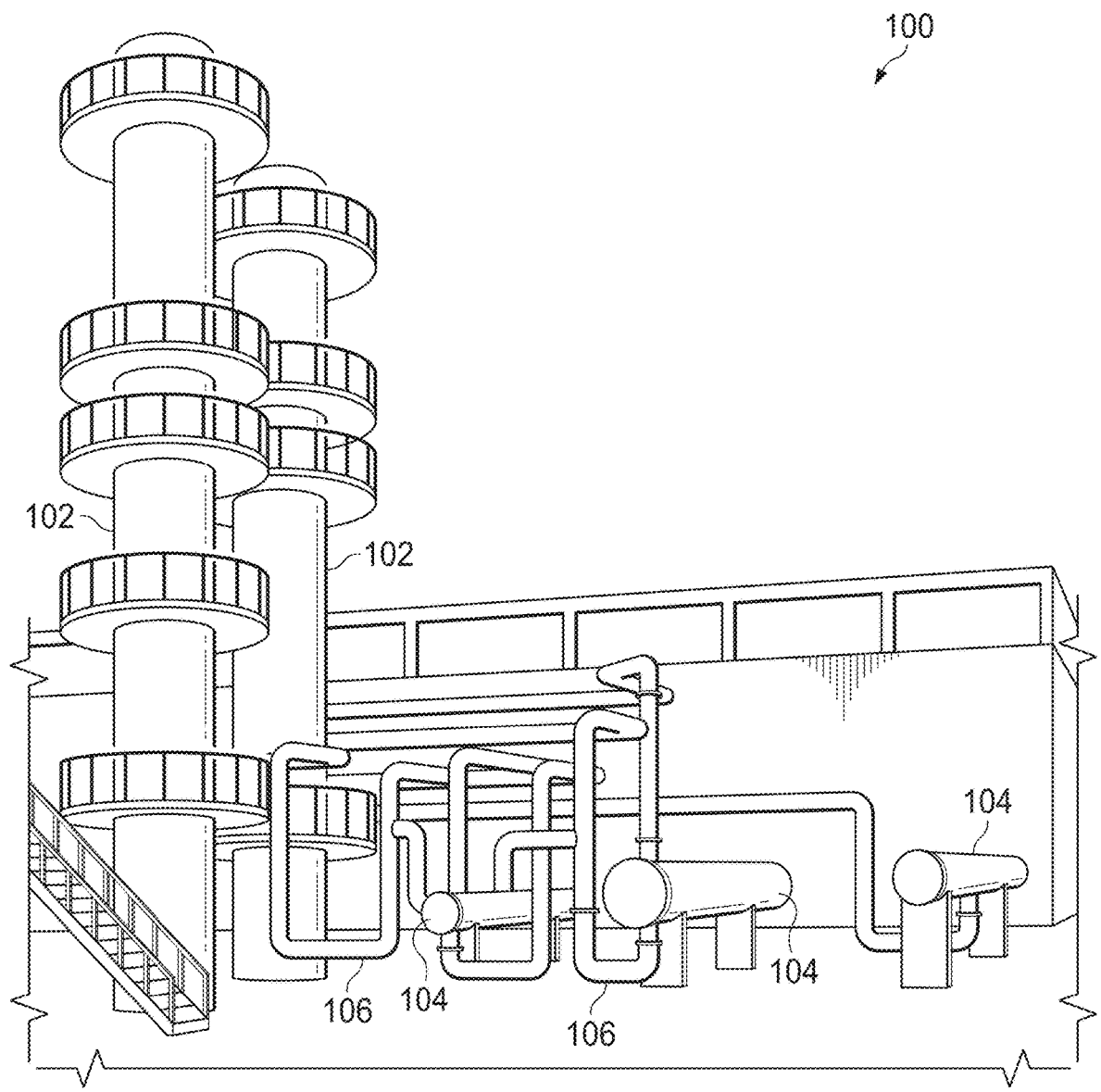
FIG. 1 is a diagram showing an example of a refinery facility including pressure vessels, heat exchangers, and piping equipment, according to some implementations of the present disclosure.

The following detailed description describes techniques for using sensors to detect High Temperature Hydrogen Attack (HTHA) conditions in oil and gas (O&G) operations. Various modifications, alterations, and permutations of the disclosed implementations can be made and will be readily apparent to those of ordinary skill in the art, and the general principles defined may be applied to other implementations and applications, without departing from the scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

Sensors can be permanently installed in susceptible locations to provide an on-stream integrity assessment of assets while the assets remain online. This technology can detect stress cracking associated with HTHA based on electromagnetic fields penetrating through the inspected surface and with the help of the pH sensor that measures the level of methane escaping through the metal for accurate HTHA presence. In some implementations, the following tools can be used.

An inspection non-destructive testing (NDT) tool can be used for online and on-demand monitoring based on the use of a micro pH rods/sensors based on metal oxide. This can be used to detect the change of pH on the surface of metal by measuring the potential voltage for early detection of symptoms related to HTHA (e.g., methane release from asset).

An inspection NDT tool can be used for online and continuous monitoring based on the use of PEC for the measurement and sizing of cracks and fissures (e.g., methane $CH_2$), which are known causes of HTHA. In another example, an inspection NDT tool can be used for online and continuous monitoring based on the integration of a metal oxide pH and PEC sensor system. In this case, the inspection NDT tool can be used to detect cracks caused by HTHA in heat exchangers, piping equipment, pressure vessels, and Naphtha Unifier/Hydro-treating reactors commonly found in the oil and gas industry.

Inspection NDT tools for online and continuous monitoring can be based on the integration of a metal oxide pH and PEC sensor system to detect stress-cracking caused by HTHA in carbon/carbon-½ molybdenum and low alloy chromium-molybdenum steels that are susceptible to HTHA.

Inspection NDT tools for online and continuous monitoring can be based on the integration of the metal oxide pH and PEC sensor system to detect stress-cracking caused by HTHA in heat-affected zones (HAZ) or the fusion line of welds.

The inspection NDT tool can be used with assets for both new and existing units in refineries and petrochemical plants known to be susceptible to HTHA (not limited to) catalytic reformers (platformer CCR/Rheniformer), diesel hydro-treaters, hydrogen plant related units operating at high temperature and pressure and hydrocrackers. Temperature indicators (e.g., magnetic contact thermocouples) can be used to monitor the continuous temperature of the targeted area during the inspection cycle.

Techniques can include the use of two phases that occur in a sequential and complementary fashion, e.g., in an integrated pH and PEC sensor system. A PEC phase can be used to target locations pre-identified by thermocouples. The PEC phase can contribute in reducing unnecessary inspections that are done by PEC alone. The pH and PEC sensor system can be used in an integrated pH and PEC sensor system for online monitoring integrated on physically reconfigurable (flexible and stretchable) skin that is applicable in harsh environments (e.g., in high temperatures). The integrated pH and PEC sensor system can provide risk-based inspection (RBI) of the HTHA damage mechanism and continuous monitoring of asset integrity. Inspection data collected from the hybrid sensory system can be communicated over a wireless communication mode (e.g., based on Wi-Fi) to an onsite computer system for further processing. A swarm of flexible, stretchable hybrid pH and integrated PEC sensors can be used to increase the efficiency and speed of the inspection solution.

A sensing and inspection mechanism can be printed on a flexible and stretchable platform. The mechanism can be part of a dual sensory system concept applied externally to the asset for the detection and inspection of micro-cracks characteristic of HTHA presence (initial growth) and any other defects for assets operating at lower temperature envelop. The sensory system can provide its analysis while the asset remains online.

The sensory system can be applied and fixed at locations known to be vulnerable to HTHA (e.g., Heat Affected Zones (HAZ) and the fusion lines of welds) and can provide continuous measurements. The adhesive material can be based on a high-temperature air-drying refractory material that can withstand the operational temperature of the asset being monitored. The placement of the sensors is not limited to the HAZ and weld fusion zones. For example, the sensors can be applied at any location throughout the external surface of the asset to monitor various suspected locations.

This sensory system can be integrated on a physically reconfigurable (e.g., flexible and stretchable) skin and applied in a harsh environment (e.g., high temperatures up to 900° F. (480° C.)). The advanced material used in this case can be a composite of the water-containing hydrogel and a metal-carbide compound known as MXene. MXenes are highly conductive materials, which have demonstrated state-of-the-art performance in electromagnetic sensing, chemical sensing, and energy storage. MXenes have suitable physics and chemistry-based properties for this application of high temperature (e.g., can be used in applications of up to 600° C.), are suitable for adhesion to metallic surfaces, and have ideal properties for electronic sensory based systems. The main properties of the proposed advanced material for the present disclosure include, but are not limited to, Mechanical Strength, Flexibility, Heat Insulation, and Electronic Properties Techniques of the present disclosure can be used to integrate a sensing solution that can provide conditioning monitoring for online assets that are susceptible to HTHA. This sensor system can determine the presence of existing and early stage HTHA through examination of crack formations. This can be done by using electro-magnetic sensors (e.g., Pulsed Eddy Current (PEC)) and pH sensors to measure methane escaping through the asset steel. Surface temperatures can be measured using a thermocouple to help identify the susceptibility level of the surface. The techniques can be integrated as an array of sensors on a single adhesive flexible and stretchable platform that can withstand harsh temperature environments. Different sensor types can be used.

Figure 4:
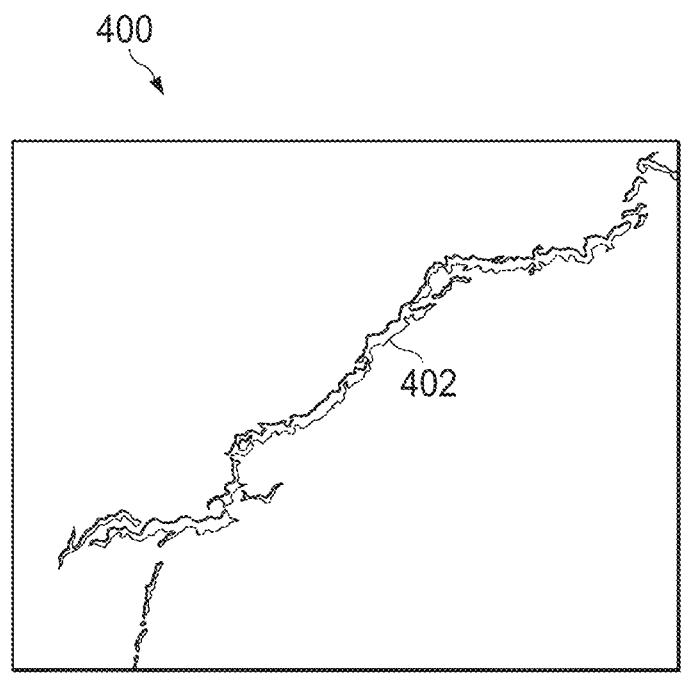
FIG. 4 is a diagram illustrating an example of micro-cracks between large metallic surfaces affected by the HTHA, according to some implementations of the present disclosure.

Electromagnetic sensors that are used can include a flexible electromagnetic (EM) array sensor, which can be a PEC, electromagnetic acoustic transducer (EMAT), or any other electromagnetic probe. The sensor can include a set of spiral sensor coils that are used to measure micro-cracks between large metallic surfaces affected by the HTHA and as shown in FIG. 4. An advantage of an array-based system is that there is no need for scanning a single probe mechanically over the asset surface. Multiple elements, uniformly spaced, can provide a direct two-dimensional (2D) scan. This, in turn, can reduce the requirement for accurate and fast scanning and allows comparison between the responses from different array elements. Generally, the elementary coils used in an EM array have characteristics similar to those of standard coils in their size, sensitivity, and accuracy. This can provide an increase in scan speed and higher quality and reliable diagnosis.

FIG. 1 is a diagram showing an example of a refinery facility 100 including pressure vessels 102, heat exchangers 104, and piping equipment 106, according to some implementations of the present disclosure. The refinery facility 100 may be susceptible to HTHA damage, for example.

Figure 2C:
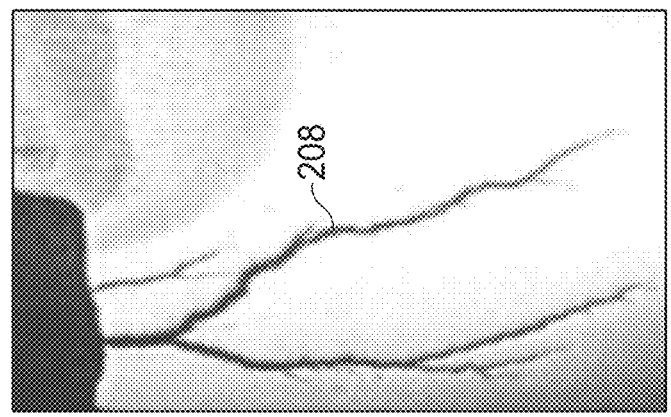
FIGS. 2A-2C are images showing examples of stress cracks corresponding to a high temperature hydrogen attack (HTHA), according to some implementations of the present disclosure.
Figure 2B:
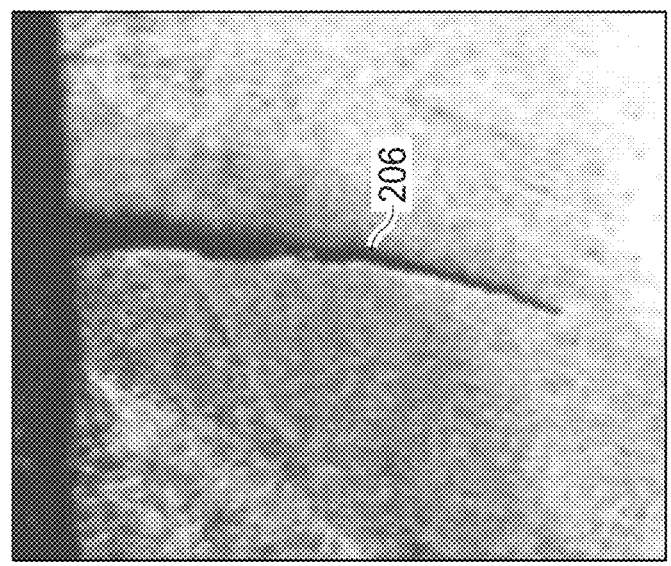
Figure 2A:
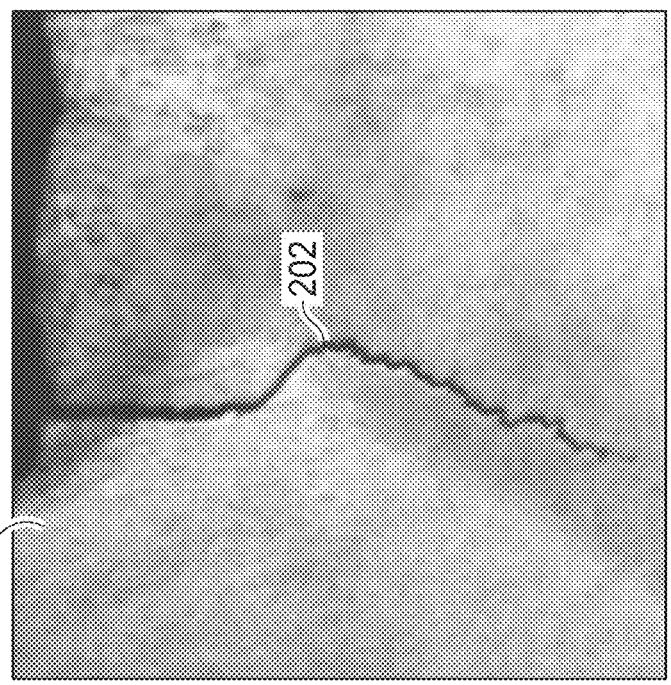

FIGS. 2A-2C are images showing examples of stress cracks 202, 206, and 208 corresponding to a HTHA 204, according to some implementations of the present disclosure.

Figure 3:
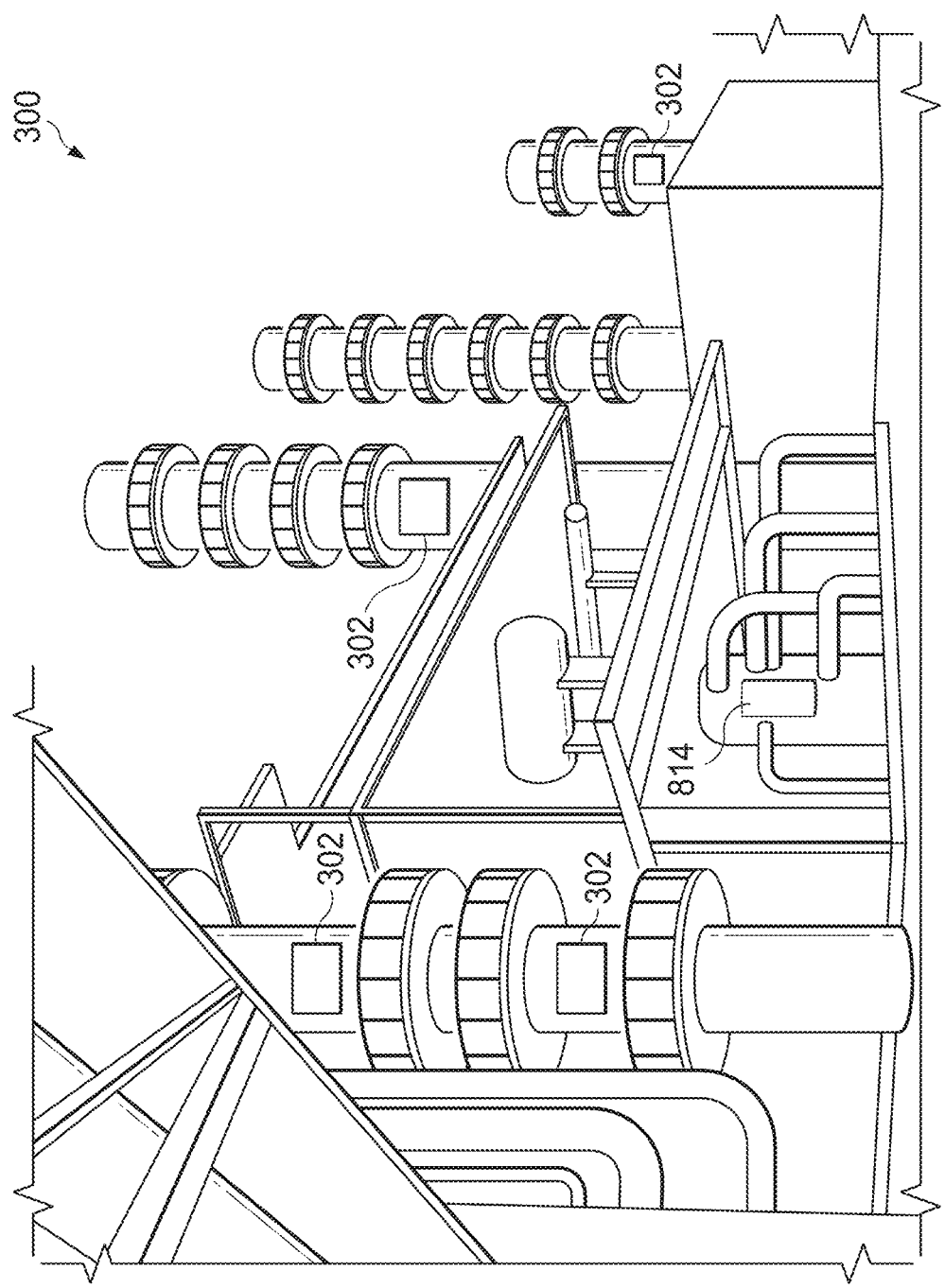
FIG. 3 is a diagram illustrating an example of an HTHA flexible hybrid sensory system, according to some implementations of the present disclosure.

FIG. 3 is a diagram illustrating an example of an HTHA flexible hybrid sensory system 300, according to some implementations of the present disclosure. Permanent sensors 302 are placed at various locations of the HTHA flexible hybrid sensory system 300.

Groups of pH sensors can be used to measure hydrogen-ion activity of corroding metal, indicating a susceptibility level expressed as pH. The pH sensor can measure the difference in electrical potential between a pH electrode and a reference electrode. The sensory system can integrate micro pH rods/sensors based on metal oxide to detect the change of pH on the surface of metal by measuring the potential voltage.

Figure 6:
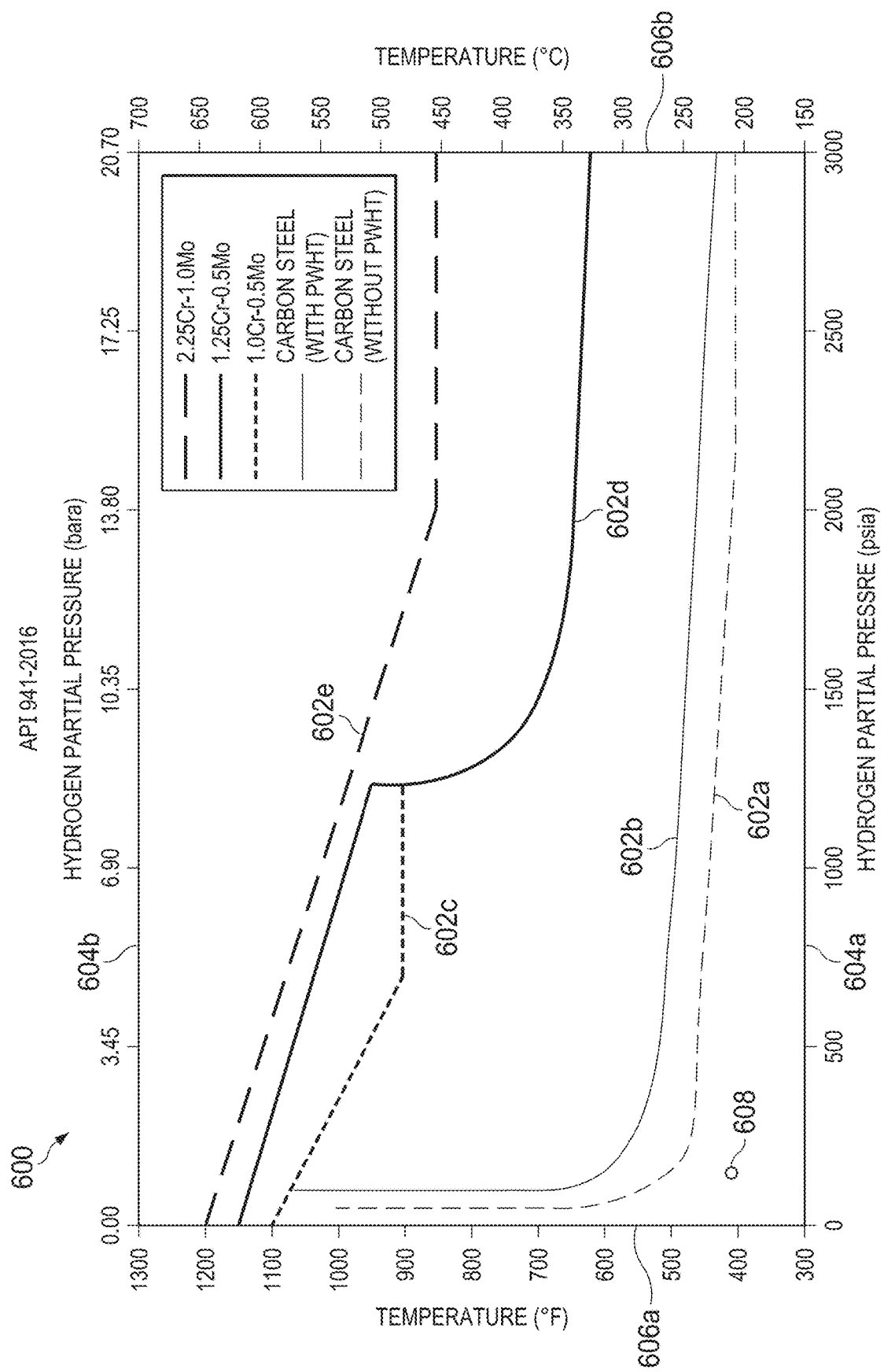
FIG. 6 is a graph representing an HTHA susceptibility calculator showing positions of operating data versus Nelson curves, according to some implementations of the present disclosure.

Temperature sensors can be used to measure temperature profiles for a local spot and determine the HTHA susceptibility level that will be used to evaluate the position of representative operating conditions of an existing equipment related to the appropriate Nelson curve as shown in FIGS. 5-6.

FIG. 4 is a diagram 400 illustrating an example of micro-cracks 402 between large metallic surfaces affected by the HTHA, according to some implementations of the present disclosure.

FIG. 5 is a diagram illustrating a representation 500 of American Petroleum Institute (API) recommended practice (RP) 941 Nelson curves, according to some implementations of the present disclosure. The representation 500 includes a graph characterizing HTHA susceptibility based on an evaluation of pressure and temperature. The evaluation considers the position of representative operating conditions of an existing equipment or pipe related to the appropriate Nelson Curve. Information on the representation 500 is plotted relative to a partial pressure of $H_2$ 502 and a temperature 504. Regions 506 of the representation 500 show areas of no hydrogen attack, based on lower pressures and temperature. The regions 506 are separated from the rest of the representation 500 using a pressure asymptote 508a (e.g., at a pressure of 50 pounds per square inch absolute (psia)) and a temperature asymptote 508b (e.g., 205° C. (or 400° F.)). Lines 510, 512, 514, and 516 on the representation 500 indicate susceptibilities of different metals, including carbon steel and different steel alloys containing various amounts of Chromium (Cr) and Molybdenum (Mo). Arrow 518 indicates an increasing level of protection from susceptibilities, including by the addition of Vanadium (V) to the alloy(s). Hydrcrackers (HCUs) 520 are also shown.

FIG. 6 is a graph 600 representing an HTHA susceptibility calculator showing positions of operating data versus Nelson curves, according to some implementations of the present disclosure. The graph 600 includes plots 602a-602e showing different types of steel including with and without post weld heat treatment (PWHT) and using different steel alloys. The plots 602a-602e are plotted relative to axes of hydrogen partial pressure in psia 604a and barometric (baro) pressure 604b, temperature in ° F. 606a, and temperature in ° C. 606b. Point 608 is relative below non-post weld heat treatments (non-PWHTs) for steels on hydrogen service.

Table 1 provides examples of susceptibility criteria that can be used in an HTHA susceptibility calculator, such as in FIG. 6:

TABLE 1

HTHA Susceptibility Criteria

| Susceptibility Level | Conditions |
| --- | --- |
| High Susceptibility | At or above existing Nelson Curve limits |
| Medium Susceptibility | Up to and including 14° C. (25° F.) below existing Nelson Curves limits |
| Low Susceptibility | Between 14° C. (25° F.) and 28° C. (50° F.) below existing Nelson Curve limits |
| Not Susceptibility | More than 28° C. (50° F.) below existing Nelson Curve limits |

Figure 7:
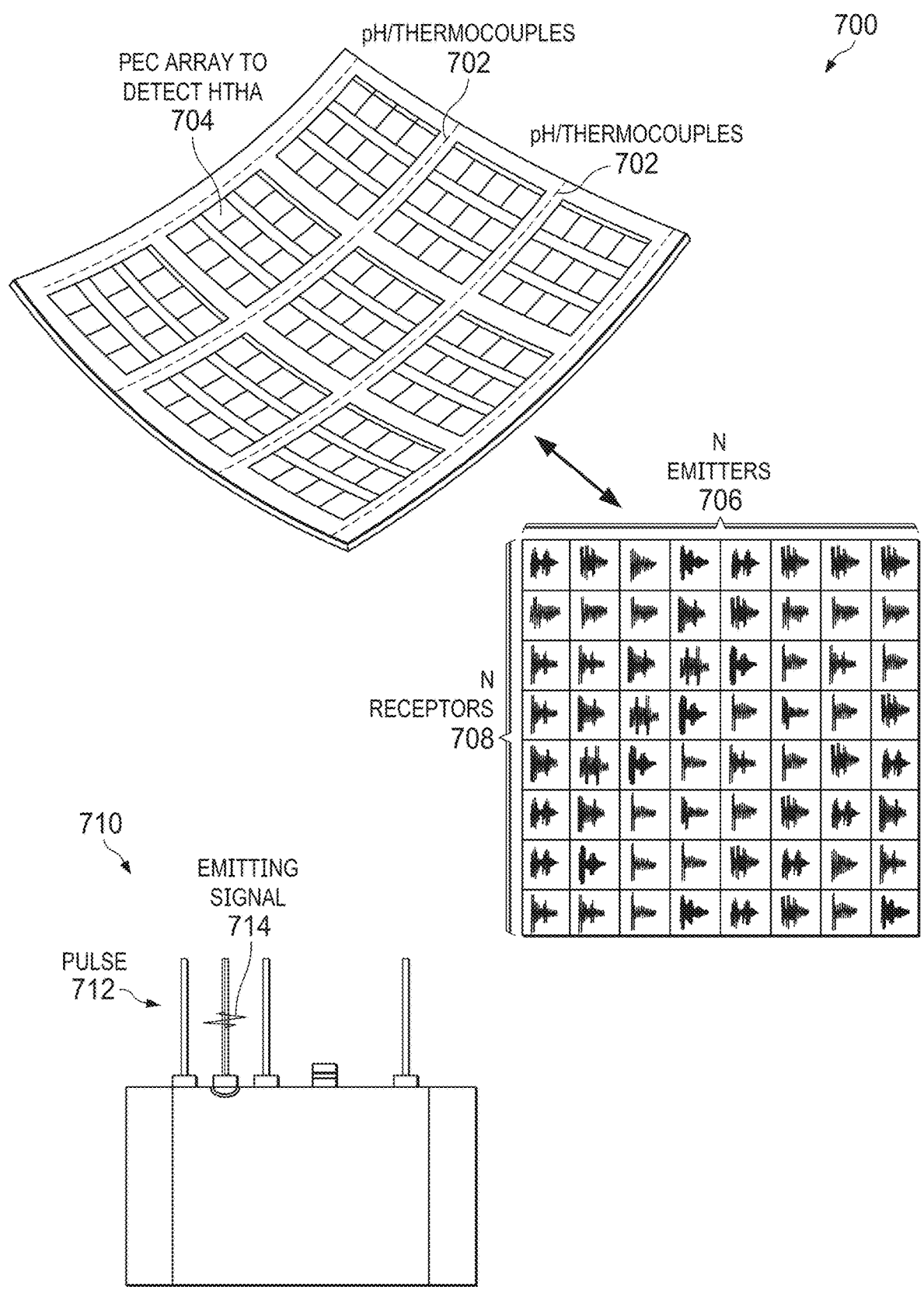
FIG. 7 is a diagram showing an example of a hybrid sensory system for early detection of HTHA, according to some implementations of the present disclosure.

FIG. 7 is a diagram showing an example of a hybrid sensory system 700 for early detection of HTHA, according to some implementations of the present disclosure. The hybrid sensory system 700 can use sensor fusion of EM and pH/thermocouples sensors 702 and a PEC array 704, for example. Each cell in the array can include N emitters 706 and N receptors 708. A side view 710 of the sensor shows an example of receiving a pulse 712 and emitting a signal 714. Receivers and emitters shown in the side view 710 work simultaneously for better mapping and accuracy in the early detection of HTHA.

Using the hybrid sensory system 700 can provide a compact and fully integrated sensory system that includes combinations of previously described sensor types, providing an improved solution for the detection of HTHA micro-cracks. This can be accomplished by allowing for the measurement of surface temperature and pH monitoring simultaneously in addition to the continuous monitoring of the crack propagation.

Implementations of the present disclosure can include the use of a permanent adhesive for affixing sensors to the equipment at selected localized spots using high-temperature air-drying refractory adhesive material for continuously monitoring and detection solution. FIG. 7 shows an example implementation of a combination of thermocouples and pH sensors to capture the surface temp/pH reading, while simultaneously detecting HTHA micro-cracks to reduce detection and processing time as compared to performing each task separately. Some implementations can use a single type of thermocouples or pH probe instead of many. PEC, EMAT, or any other electromagnetic probe can be used to detect the effect of HTHA micro-cracks.

Figure 8:
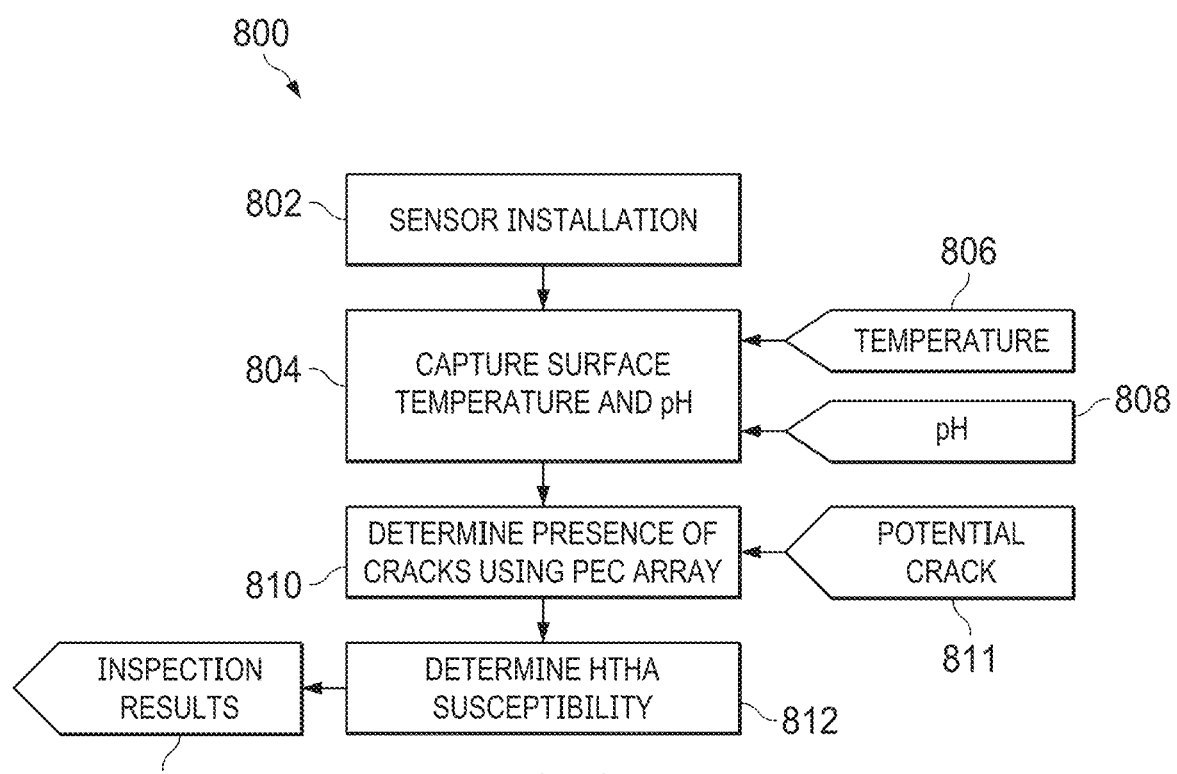
FIG. 8 is a flow chart of an example of a workflow for using an HTHA hybrid sensory system to inspect assets susceptible to HTHA corrosion, according to some implementations of the present disclosure.

FIG. 8 is a flow chart of an example of a workflow 800 for using an HTHA hybrid sensory system to inspect assets susceptible to HTHA corrosion, according to some implementations of the present disclosure. The workflow 800 provides a measurement process for inspection of micro-cracking and HTHA detection.

At 802, sensor installation is performed, including identification of a selected location by field inspection and engineers. The selected location is made to consider that hybrid pads can be permanently installed to susceptible spots of equipment base metal based on equipment history.

At 804, surface temperature 806 and pH 808 are captured. The process includes a fusion sensory technique in which a surface temperature is collected, and a measurement is made of any methane presence escaping from the external surface on the metal.

At 810, the presence of cracks is determined. For example, the PEC array sensor can be used to collect data and indicate potential cracks 811 (e.g., micro-cracks) and initial growth at the locations of the mounted pads.

At 812, HTHA susceptibility is determined. Collected data can be analyzed in order to map out potential HTHA cracks and determine early signs of methane formation.

At 814, an inspection result and assessment are generated. The final analysis can be utilized to provide assessment reports indicating the possibility of cracks propagation and the presence of fissuring inside the base metal.

Figure 9:
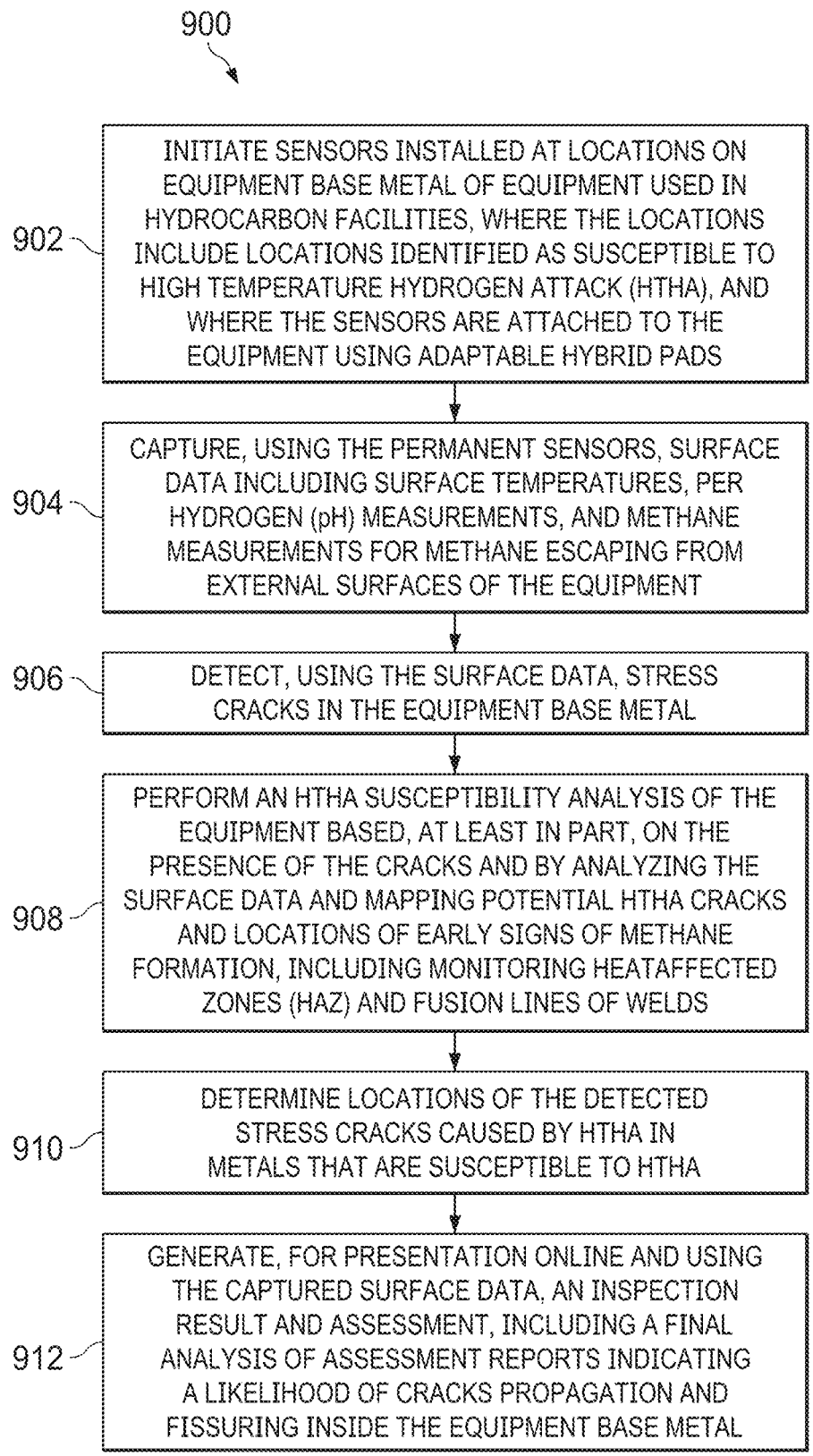
FIG. 9 is a flowchart of an example of a method for generating an inspection result and assessment for HTHA susceptibility, according to some implementations of the present disclosure.

FIG. 9 is a flowchart of an example of a method 900 for generating an inspection result and assessment for HTHA susceptibility, according to some implementations of the present disclosure. For clarity of presentation, the description that follows generally describes method 900 in the context of the other figures in this description. However, it will be understood that method 900 can be performed, for example, by any suitable system, environment, software, and hardware, or a combination of systems, environments, software, and hardware, as appropriate. In some implementations, various steps of method 900 can be run in parallel, in combination, in loops, or in any order.

At 902, sensors are initiated that are installed at locations on equipment base metal of equipment used in hydrocarbon facilities. The locations include locations identified as susceptible to high temperature hydrogen attack (HTHA). The sensors are attached to the equipment using adaptable hybrid pads. The sensors can include a PEC array, for example. The sensors can include permanently attached sensors. In some implementations, locations for attaching sensors can be determined based at least on an equipment history of the equipment, and can include locations that are susceptible to HTHA. From 902, method 900 proceeds to 904.

At 904, surface data is captured using the permanent sensors. The surface data includes surface temperatures, per hydrogen (pH) measurements, and methane measurements for methane escaping from external surfaces of the equipment. Capturing the surface data can include using wireless communications of the surface data from the sensors to an onsite computer system. Capturing the surface data includes recording, with the surface data for each sensor, a location on the equipment on which the sensor is installed. The permanent sensors can be attached to inspected surfaces that are susceptible for HTHA, with mapping occurring during the inspection survey to indicate the location of the crack within the area. From 904, method 900 proceeds to 906.

At 906, stress cracks in the equipment base metal are detected using the surface data. The cracks associated with HTHA are usually at a micro level. From 906, method 900 proceeds to 908.

At 908, an HTHA susceptibility analysis of the equipment is performed based, at least in part, on the presence of the cracks and by analyzing the surface data and mapping potential HTHA cracks and locations of early signs of methane formation, including monitoring heat-affected zones (HAZ) and fusion lines of welds. Performing the HTHA susceptibility analysis of the equipment can include analyzing carbon/carbon-½ molybdenum and low alloy chromium-molybdenum steels. From 908, method 900 proceeds to 910.

At 910, locations of the detected stress cracks caused by HTHA in metals that are susceptible to HTHA are determined. The locations of the cracks can be reported using C-map electromagnetic gradients that visually point out the areas of the cracks. From 910, method 900 proceeds to 912.

At 912, an inspection result and assessment are generated using the captured surface data for presentation online, including a final analysis of assessment reports indicating a likelihood of cracks propagation and fissuring inside the equipment base metal. After 912, method 900 can stop.

In some implementations, in addition to (or in combination with) any previously-described features, techniques of the present disclosure can include the following. Customized user interfaces can present intermediate or final results of the above described processes to a user. The presented information can be presented in one or more textual, tabular, or graphical formats, such as through a dashboard. The information can be presented at one or more on-site locations (such as at an oil well or other facility), on the Internet (such as on a webpage), on a mobile application (or "app"), or at a central processing facility. The presented information can include suggestions, such as suggested changes in parameters or processing inputs, that the user can select to implement improvements in a production environment, such as in the exploration, production, and/or testing of petrochemical processes or facilities. For example, the suggestions can include parameters that, when selected by the user, can cause a change or an improvement in drilling parameters (including speed and direction) or overall production of a gas or oil well. The suggestions, when implemented by the user, can improve the speed and accuracy of calculations, streamline processes, improve models, and solve problems related to efficiency, performance, safety, reliability, costs, downtime, and the need for human interaction. In some implementations, the suggestions can be implemented in real-time, such as to provide an immediate or near-immediate change in operations or in a model. The term real-time can correspond, for example, to events that occur within a specified period of time, such as within one minute or within one second. In some implementations, values of parameters or other variables that are determined can be used automatically (such as through using rules) to implement changes in oil or gas well exploration, production/drilling, or testing. For example, outputs of the present disclosure can be used as inputs to other equipment and/or systems at a facility. This can be especially useful for systems or various pieces of equipment that are located several meters or several miles apart, or are located in different countries or other jurisdictions.

Figure 10:
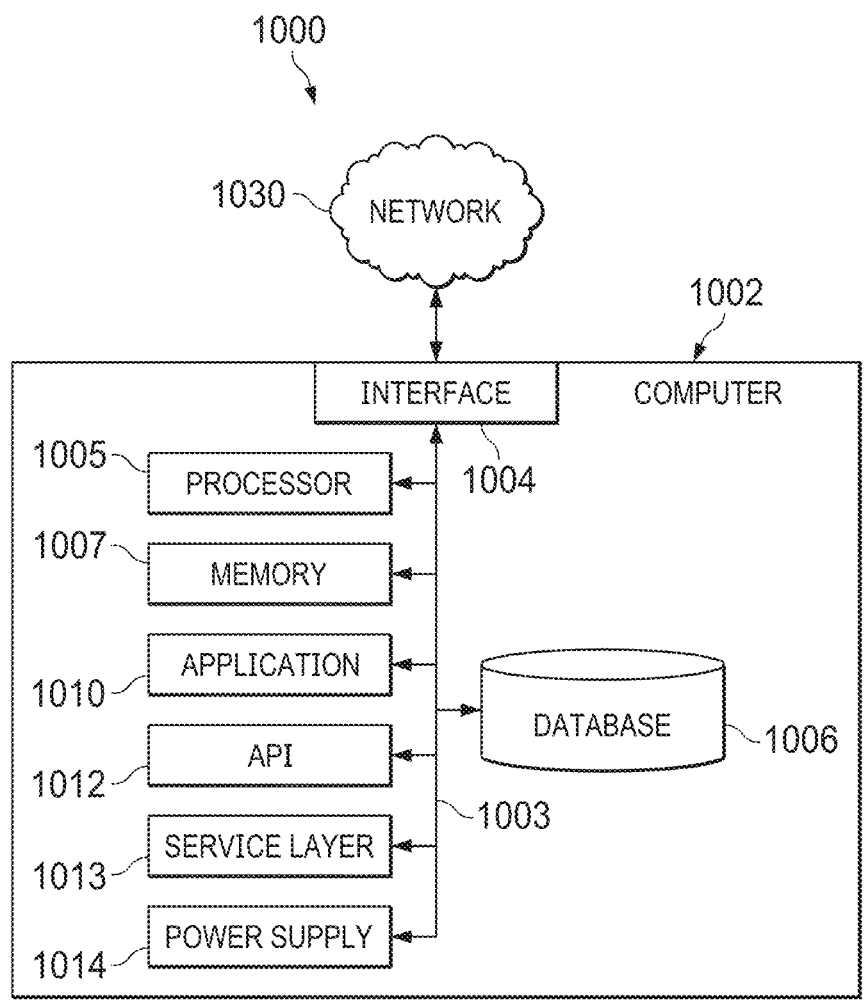
FIG. 10 is a block diagram illustrating an example computer system used to provide computational functionalities associated with described algorithms, methods, functions, processes, flows, and procedures as described in the present disclosure, according to some implementations of the present disclosure.

FIG. 10 is a block diagram of an example computer system 1000 used to provide computational functionalities associated with described algorithms, methods, functions, processes, flows, and procedures described in the present disclosure, according to some implementations of the present disclosure. The illustrated computer 1002 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 1002 can include input devices such as keypads, keyboards, and touch screens that can accept user information. Also, the computer 1002 can include output devices that can convey information associated with the operation of the computer 1002. The information can include digital data, visual data, audio information, or a combination of information. The information can be presented in a graphical user interface (UI) (or GUI).

The computer 1002 can serve in a role as a client, a network component, a server, a database, a persistency, or components of a computer system for performing the subject matter described in the present disclosure. The illustrated computer 1002 is communicably coupled with a network 1030. In some implementations, one or more components of the computer 1002 can be configured to operate within different environments, including cloud-computing-based environments, local environments, global environments, and combinations of environments.

At a top level, the computer 1002 is an electronic computing device operable to receive, transmit, process, store, and manage data and information associated with the described subject matter. According to some implementations, the computer 1002 can also include, or be communicably coupled with, an application server, an email server, a web server, a caching server, a streaming data server, or a combination of servers.

The computer 1002 can receive requests over network 1030 from a client application (for example, executing on another computer 1002). The computer 1002 can respond to the received requests by processing the received requests using software applications. Requests can also be sent to the computer 1002 from internal users (for example, from a command console), external (or third) parties, automated applications, entities, individuals, systems, and computers.

Each of the components of the computer 1002 can communicate using a system bus 1003. In some implementations, any or all of the components of the computer 1002, including hardware or software components, can interface with each other or the interface 1004 (or a combination of both) over the system bus 1003. Interfaces can use an application programming interface (API) 1012, a service layer 1013, or a combination of the API 1012 and service layer 1013. The API 1012 can include specifications for routines, data structures, and object classes. The API 1012 can be either computer-language independent or dependent. The API 1012 can refer to a complete interface, a single function, or a set of APIs.

The service layer 1013 can provide software services to the computer 1002 and other components (whether illustrated or not) that are communicably coupled to the computer 1002. The functionality of the computer 1002 can be accessible for all service consumers using this service layer. Software services, such as those provided by the service layer 1013, can provide reusable, defined functionalities through a defined interface. For example, the interface can be software written in JAVA, C++, or a language providing data in extensible markup language (XML) format. While illustrated as an integrated component of the computer 1002, in alternative implementations, the API 1012 or the service layer 1013 can be stand-alone components in relation to other components of the computer 1002 and other components communicably coupled to the computer 1002. Moreover, any or all parts of the API 1012 or the service layer 1013 can be implemented as child or sub-modules of another software module, enterprise application, or hardware module without departing from the scope of the present disclosure.

The computer 1002 includes an interface 1004. Although illustrated as a single interface 1004 in FIG. 10, two or more interfaces 1004 can be used according to particular needs, desires, or particular implementations of the computer 1002 and the described functionality. The interface 1004 can be used by the computer 1002 for communicating with other systems that are connected to the network 1030 (whether illustrated or not) in a distributed environment. Generally, the interface 1004 can include, or be implemented using, logic encoded in software or hardware (or a combination of software and hardware) operable to communicate with the network 1030. More specifically, the interface 1004 can include software supporting one or more communication protocols associated with communications. As such, the network 1030 or the interface's hardware can be operable to communicate physical signals within and outside of the illustrated computer 1002.

The computer 1002 includes a processor 1005. Although illustrated as a single processor 1005 in FIG. 10, two or more processors 1005 can be used according to particular needs, desires, or particular implementations of the computer 1002 and the described functionality. Generally, the processor 1005 can execute instructions and can manipulate data to perform the operations of the computer 1002, including operations using algorithms, methods, functions, processes, flows, and procedures as described in the present disclosure.

The computer 1002 also includes a database 1006 that can hold data for the computer 1002 and other components connected to the network 1030 (whether illustrated or not). For example, database 1006 can be an in-memory, conventional, or a database storing data consistent with the present disclosure. In some implementations, database 1006 can be a combination of two or more different database types (for example, hybrid in-memory and conventional databases) according to particular needs, desires, or particular implementations of the computer 1002 and the described functionality. Although illustrated as a single database 1006 in FIG. 10, two or more databases (of the same, different, or combination of types) can be used according to particular needs, desires, or particular implementations of the computer 1002 and the described functionality. While database 1006 is illustrated as an internal component of the computer 1002, in alternative implementations, database 1006 can be external to the computer 1002.

The computer 1002 also includes a memory 1007 that can hold data for the computer 1002 or a combination of components connected to the network 1030 (whether illustrated or not). Memory 1007 can store any data consistent with the present disclosure. In some implementations, memory 1007 can be a combination of two or more different types of memory (for example, a combination of semiconductor and magnetic storage) according to particular needs, desires, or particular implementations of the computer 1002 and the described functionality. Although illustrated as a single memory 1007 in FIG. 10, two or more memories 1007 (of the same, different, or combination of types) can be used according to particular needs, desires, or particular implementations of the computer 1002 and the described functionality. While memory 1007 is illustrated as an internal component of the computer 1002, in alternative implementations, memory 1007 can be external to the computer 1002.

The application 1008 can be an algorithmic software engine providing functionality according to particular needs, desires, or particular implementations of the computer 1002 and the described functionality. For example, application 1008 can serve as one or more components, modules, or applications. Further, although illustrated as a single application 1008, the application 1008 can be implemented as multiple applications 1008 on the computer 1002. In addition, although illustrated as internal to the computer 1002, in alternative implementations, the application 1008 can be external to the computer 1002.

The computer 1002 can also include a power supply 1014. The power supply 1014 can include a rechargeable or non-rechargeable battery that can be configured to be either user- or non-user-replaceable. In some implementations, the power supply 1014 can include power-conversion and management circuits, including recharging, standby, and power management functionalities. In some implementations, the power supply 1014 can include a power plug to allow the computer 1002 to be plugged into a wall socket or a power source to, for example, power the computer 1002 or recharge a rechargeable battery.

There can be any number of computers 1002 associated with, or external to, a computer system containing computer 1002, with each computer 1002 communicating over network 1030. Further, the terms "client," "user," and other appropriate terminology can be used interchangeably, as appropriate, without departing from the scope of the present disclosure. Moreover, the present disclosure contemplates that many users can use one computer 1002 and one user can use multiple computers 1002.

Described implementations of the subject matter can include one or more features, alone or in combination.

For example, in a first implementation, a computer-implemented method includes the following. Sensors are initiated that are installed at locations on equipment base metal of equipment used in hydrocarbon facilities. The locations include locations identified as susceptible to high temperature hydrogen attack (HTHA). The sensors are attached to the equipment using adaptable hybrid pads. Surface data is captured using the permanent sensors. The surface data includes surface temperatures, per hydrogen (pH) measurements, and methane measurements for methane escaping from external surfaces of the equipment. Stress cracks in the equipment base metal are detected using the surface data. An HTHA susceptibility analysis of the equipment is performed based, at least in part, on the presence of the cracks and by analyzing the surface data and mapping potential HTHA cracks and locations of early signs of methane formation, including monitoring heat-affected zones (HAZ) and fusion lines of welds. Locations of the detected stress cracks caused by HTHA in metals that are susceptible to HTHA are determined. An inspection result and assessment are generated using the captured surface data for presentation online, including a final analysis of assessment reports indicating a likelihood of cracks propagation and fissuring inside the equipment base metal.

The foregoing and other described implementations can each, optionally, include one or more of the following features:

A first feature, combinable with any of the following features, where the sensors include a pulsed eddy current (PEC) array.

A second feature, combinable with any of the previous or following features, where the sensors include permanently attached sensors.

A third feature, combinable with any of the previous or following features, where capturing the surface data includes using wireless communications of the surface data from the sensors to an onsite computer system.

A fourth feature, combinable with any of the previous or following features, where performing the HTHA susceptibility analysis of the equipment includes analyzing carbon/carbon-½ molybdenum and low alloy chromium-molybdenum steels.

A fifth feature, combinable with any of the previous or following features, where capturing the surface data includes recording, with the surface data for each sensor, a location on the equipment on which the sensor is installed.

A sixth feature, combinable with any of the previous or following features, the method further including determining, based at least on an equipment history of the equipment, that the locations include locations that are susceptible to HTHA.

In a second implementation, a non-transitory, computer-readable medium stores one or more instructions executable by a computer system to perform operations including the following. Sensors are initiated that are installed at locations on equipment base metal of equipment used in hydrocarbon facilities. The locations include locations identified as susceptible to high temperature hydrogen attack (HTHA). The sensors are attached to the equipment using adaptable hybrid pads. Surface data is captured using the permanent sensors. The surface data includes surface temperatures, per hydrogen (pH) measurements, and methane measurements for methane escaping from external surfaces of the equipment. Stress cracks in the equipment base metal are detected using the surface data. An HTHA susceptibility analysis of the equipment is performed based, at least in part, on the presence of the cracks and by analyzing the surface data and mapping potential HTHA cracks and locations of early signs of methane formation, including monitoring heat-affected zones (HAZ) and fusion lines of welds. Locations of the detected stress cracks caused by HTHA in metals that are susceptible to HTHA are determined. An inspection result and assessment are generated using the captured surface data for presentation online, including a final analysis of assessment reports indicating a likelihood of cracks propagation and fissuring inside the equipment base metal.

The foregoing and other described implementations can each, optionally, include one or more of the following features:

A first feature, combinable with any of the following features, where the sensors include a pulsed eddy current (PEC) array.

A second feature, combinable with any of the previous or following features, where the sensors include permanently attached sensors.

A third feature, combinable with any of the previous or following features, where capturing the surface data includes using wireless communications of the surface data from the sensors to an onsite computer system.

A fourth feature, combinable with any of the previous or following features, where performing the HTHA susceptibility analysis of the equipment includes analyzing carbon/carbon-½ molybdenum and low alloy chromium-molybdenum steels.

A fifth feature, combinable with any of the previous or following features, where capturing the surface data includes recording, with the surface data for each sensor, a location on the equipment on which the sensor is installed.

A sixth feature, combinable with any of the previous or following features, the operations further including determining, based at least on an equipment history of the equipment, that the locations include locations that are susceptible to HTHA.

In a third implementation, a computer-implemented system includes one or more processors and a non-transitory computer-readable storage medium coupled to the one or more processors and storing programming instructions for execution by the one or more processors. The programming instructions instruct the one or more processors to perform operations including the following. Sensors are initiated that are installed at locations on equipment base metal of equipment used in hydrocarbon facilities. The locations include locations identified as susceptible to high temperature hydrogen attack (HTHA). The sensors are attached to the equipment using adaptable hybrid pads. Surface data is captured using the permanent sensors. The surface data includes surface temperatures, per hydrogen (pH) measurements, and methane measurements for methane escaping from external surfaces of the equipment. Stress cracks in the equipment base metal are detected using the surface data. An HTHA susceptibility analysis of the equipment is performed based, at least in part, on the presence of the cracks and by analyzing the surface data and mapping potential HTHA cracks and locations of early signs of methane formation, including monitoring heat-affected zones (HAZ) and fusion lines of welds. Locations of the detected stress cracks caused by HTHA in metals that are susceptible to HTHA are determined. An inspection result and assessment are generated using the captured surface data for presentation online, including a final analysis of assessment reports indicating a likelihood of cracks propagation and fissuring inside the equipment base metal.

The foregoing and other described implementations can each, optionally, include one or more of the following features:

A first feature, combinable with any of the following features, where the sensors include a pulsed eddy current (PEC) array.

A second feature, combinable with any of the previous or following features, where the sensors include permanently attached sensors.

A third feature, combinable with any of the previous or following features, where capturing the surface data includes using wireless communications of the surface data from the sensors to an onsite computer system.

A fourth feature, combinable with any of the previous or following features, where performing the HTHA susceptibility analysis of the equipment includes analyzing carbon/carbon-½ molybdenum and low alloy chromium-molybdenum steels.

A fifth feature, combinable with any of the previous or following features, where capturing the surface data includes recording, with the surface data for each sensor, a location on the equipment on which the sensor is installed.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/−R, DVD-RAM, DVD-ROM, HD-DVD, and BLU-RAY.

The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at the application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A computer-implemented method, comprising:
   initiating sensors installed at locations on equipment base metal of equipment used in hydrocarbon facilities, wherein the locations comprise locations identified as susceptible to high temperature hydrogen attack (HTHA), and wherein the sensors are attached to the equipment using adaptable hybrid pads, the sensors comprising an electromagnetic sensor, thermocouple sensor, and a pH sensor;
   capturing, using the sensors, surface data comprising surface temperatures, per hydrogen (pH) measurements, and methane measurements for methane escaping from external surfaces of the equipment;
   detecting, using the surface data, stress cracks in the equipment base metal;
   performing an HTHA susceptibility analysis of the equipment based, at least in part, on a presence of the stress cracks and by analyzing the surface data and mapping potential HTHA cracks and locations of early signs of methane formation, comprising monitoring heat-affected zones (HAZ) and fusion lines of welds;
   determining locations of the stress cracks caused by HTHA in metals that are susceptible to HTHA;
   generating, for presentation online and using the surface data, an inspection result and assessment, comprising a final analysis of assessment reports indicating a likelihood of crack propagation and fissuring inside the equipment base metal; and
   automatically implement changes in oil or gas well production in view of the likelihood of the crack propagation and the fissuring inside the equipment base metal.

2. The computer-implemented method of claim 1, wherein the sensors comprise a pulsed eddy current (PEC) array.

3. The computer-implemented method of claim 1, wherein the sensors comprise permanently attached sensors.

4. The computer-implemented method of claim 1, wherein capturing the surface data comprises using wireless communications of the surface data from the sensors to an onsite computer system.

5. The computer-implemented method of claim 1, wherein performing the HTHA susceptibility analysis of the equipment comprises analyzing carbon/carbon-½ molybdenum and low alloy chromium-molybdenum steels.

6. The computer-implemented method of claim 1, wherein capturing the surface data comprises recording, with the surface data for each sensor, a location on the equipment on which the sensor is installed.

7. The computer-implemented method of claim 1, further comprising:
determining, based at least on an equipment history of the equipment, that the locations comprise locations that are susceptible to HTHA.

8. A non-transitory, computer-readable medium storing one or more instructions executable by a computer system to perform operations comprising:
initiating sensors installed at locations on equipment base metal of equipment used in hydrocarbon facilities, wherein the locations comprise locations identified as susceptible to high temperature hydrogen attack (HTHA), and wherein the sensors are attached to the equipment using adaptable hybrid pads, the sensors comprising an electromagnetic sensor, thermocouple sensor, and a pH sensor;
capturing, using the sensors, surface data comprising surface temperatures, per hydrogen (pH) measurements, and methane measurements for methane escaping from external surfaces of the equipment;
detecting, using the surface data, stress cracks in the equipment base metal;
performing an HTHA susceptibility analysis of the equipment based, at least in part, on a presence of the stress cracks and by analyzing the surface data and mapping potential HTHA cracks and locations of early signs of methane formation, comprising monitoring heat-affected zones (HAZ) and fusion lines of welds;
determining locations of the stress cracks caused by HTHA in metals that are susceptible to HTHA;
generating, for presentation online and using the surface data, an inspection result and assessment, comprising a final analysis of assessment reports indicating a likelihood of crack propagation and fissuring inside the equipment base metal; and
automatically implement changes in oil or gas well production in view of the likelihood of the crack propagation and the fissuring inside the equipment base metal.

9. The non-transitory, computer-readable medium of claim 8, wherein the sensors comprise a pulsed eddy current (PEC) array.

10. The non-transitory, computer-readable medium of claim 8, wherein the sensors comprise permanently attached sensors.

11. The non-transitory, computer-readable medium of claim 8, wherein capturing the surface data comprises using wireless communications of the surface data from the sensors to an onsite computer system.

12. The non-transitory, computer-readable medium of claim 8, wherein performing the HTHA susceptibility analysis of the equipment comprises analyzing carbon/carbon-½ molybdenum and low alloy chromium-molybdenum steels.

13. The non-transitory, computer-readable medium of claim 8, wherein capturing the surface data comprises s recording, with the surface data for each sensor, a location on the equipment on which the sensor is installed.

14. The non-transitory, computer-readable medium of claim 8, the operations further comprising:
determining, based at least on an equipment history of the equipment, that the locations comprise locations that are susceptible to HTHA.

15. A computer-implemented system, comprising:
one or more processors; and
a non-transitory computer-readable storage medium coupled to the one or more processors and storing programming instructions for execution by the one or more processors, the programming instructions instructing the one or more processors to perform operations comprising:
initiating sensors installed at locations on equipment base metal of equipment used in hydrocarbon facilities, wherein the locations comprise locations identified as susceptible to high temperature hydrogen attack (HTHA), and wherein the sensors are attached to the equipment using adaptable hybrid pads, the sensors comprising an electromagnetic sensor, thermocouple sensor, and a pH sensor;
capturing, using the sensors, surface data comprising surface temperatures, per hydrogen (pH) measurements, and methane measurements for methane escaping from external surfaces of the equipment;
detecting, using the surface data, stress cracks in the equipment base metal;
performing an HTHA susceptibility analysis of the equipment based, at least in part, on a presence of the stress cracks and by analyzing the surface data and mapping potential HTHA cracks and locations of early signs of methane formation, comprising monitoring heat-affected zones (HAZ) and fusion lines of welds;
determining locations of the stress cracks caused by HTHA in metals that are susceptible to HTHA;
generating, for presentation online and using the surface data, an inspection result and assessment, comprising a final analysis of assessment reports indicating a likelihood of crack propagation and fissuring inside the equipment base metal; and
automatically implement changes in oil or gas well production in view of the likelihood of the crack propagation and the fissuring inside the equipment base metal.

16. The computer-implemented system of claim 15, wherein the sensors comprise a pulsed eddy current (PEC) array.

17. The computer-implemented system of claim 15, wherein the sensors comprise permanently attached sensors.

18. The computer-implemented system of claim 15, wherein capturing the surface data comprises using wireless communications of the surface data from the sensors to an onsite computer system.

19. The computer-implemented system of claim 15, wherein performing the HTHA susceptibility analysis of the equipment comprises analyzing carbon/carbon-½ molybdenum and low alloy chromium-molybdenum steels.

20. The computer-implemented system of claim 15, wherein capturing the surface data comprises recording, with the surface data for each sensor, a location on the equipment on which the sensor is installed.

* * * * *